United States Patent [19]

Makino et al.

[11] Patent Number: 5,869,526

[45] Date of Patent: Feb. 9, 1999

[54] δ-(S-METHYLISOTHIOUREIDO)-L-NORVALINE THERAPEUTIC FOR CEREBROVASCULAR DISEASES HAVING NITRIC OXIDE SYNTHASE INHIBITING FACTOR

[75] Inventors: Toshihiko Makino; Toshiaki Nagafuji, both of Shizuoka-ken, Japan

[73] Assignee: Chugai Seiyaku Kabushiki Kaisha, Tokyo, Japan

[21] Appl. No.: 696,866

[22] PCT Filed: Feb. 23, 1995

[86] PCT No.: PCT/JP95/00265

§ 371 Date: Aug. 21, 1996

§ 102(e) Date: Aug. 21, 1996

[87] PCT Pub. No.: WO95/22968

PCT Pub. Date: Aug. 31, 1995

[30] Foreign Application Priority Data

Feb. 25, 1994 [JP] Japan ............................ 6-66386
Aug. 12, 1994 [JP] Japan .......................... 6-222396

[51] Int. Cl.$^6$ .................................................. A61K 31/21

[52] U.S. Cl. .................................................. 514/508; 558/5

[58] Field of Search .................................. 514/508; 558/5

[56] References Cited

U.S. PATENT DOCUMENTS 5,364,881  11/1994  Griffith et al. ........................ 514/508

*Primary Examiner*—Michael G. Ambrose
*Attorney, Agent, or Firm*—Browdy and Neimark

[57] ABSTRACT

Compound represented by the formula (I):

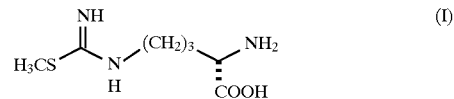

or pharmaceutically acceptable salts thereof, as well as therapeutics for cerebrovascular diseases containing such compounds or salts as an active ingredient. The compounds are capable of selective inhibition of nitric oxide synthase in neurons and, hence, are useful as the active ingredient of therapeutics for cerebrovascular diseases.

1 Claim, 3 Drawing Sheets

3δ-(S-METHYLISOTHIOUREIDO)-L-NORVALINE THERAPEUTIC FOR CEREBROVASCULAR DISEASES HAVING NITRIC OXIDE SYNTHASE INHIBITING FACTOR

TECHNICAL FIELD

This invention relates to amino acid derivatives, more particularly to δ-(S-methylisothioureido)-L-norvaline which has a nitric oxide synthase (NOS) inhibiting action and which inhibits the formation of nitric oxide (NO) so as to prove effective against the pathology of cerebrovascular diseases in the manifestation of which excess NO or NO metabolites are speculated to play an important role. The invention also relates to preventives and therapeutics of such cerebrovascular diseases that comprise the δ-(S-methylisothioureido)-L-norvaline or pharmaceutically acceptable salts thereof as an effective ingredient.

BACKGROUND ART

Recent studies have revealed that NO, which is at least one of the endothelium-derived relaxing factors (EDRF) (Nature, 327, 524–526, 1987; Nature, 333, 664–666, 1988), not only has a vasodilation effect and a platelet aggregation and adhesion inhibiting effect but also plays an important role in the maintenance of biological functions as an intra-/inter-cellular signaling molecule. (Trends Pharmacol. 10, 428–431, 1989; Trends Neurosci. 14, 29–39, 1987; Trends Biochem. 16, 81–83, 1991; Trends Neurosci. 13, 1–6, 1992; Trends Pharmacol. 12, 130–131, 1991; Trends Pharmacol. 12, 87–88, 1991; Trends Pharmacol. 12, 125–128, 1991).

It has also been established that NO is produced not only from endothelial cells but also from other cells such as neurons, glial cells and macrophages and at least three distinct clones encoding independent NOS enzymes have been isolated (Nature, 351, 714–718, 1991; Proc. Natl. Acad. Sci. USA, 89, 11141–11145, 1992; Proc. Natl. Acad. Sci. USA, 89, 6348–6352, 1992; FEBS Lett., 307, 287–293, 1992; J. Clin. Inv., 90, 2092–2096, 1992; Science, 256, 225–228, 1992; J. Biol. Chem., 267, 6370–6374, 1992; Proc. Natl. Acad. Sci. USA, 90, 11419–11423, 1993; Biochem., 32, 11600–11605, 1993; Proc. Natl. Acad. Sci. USA, 90, 3491–3495, 1993; FEBS Lett., 316, 175–180, 1993; Biochem. Biophys. Res. Commun., 191, 89–94, 1993; Proc. Natl. Acad. Sci. USA, 89, 6711–6715, 1992; Biochem. Biophys. Res. Commun., 191, 767–774, 1993; Proc. Natl. Acad. Sci. USA, 90, 9730–9734, 1993).

It is also interesting to note that the pathophysiological role of NO has been unravelled at an accelerated rate (Pharmacol. Rev., 43, 109–142, 1991; Neurol. Prog., 32, 197–311, 1992; FASEB J., 6, 3051–3064, 1992).

Among the NOS inhibitors, $N^G$-nitro-L-arginine (L-NNA) has been found to be capable of ameliorating ischemic cerebral infarction and edema (Eur. J. Pharmacol. 204, 339–340, 1991; Neurosci. Lett., 147, 159–162, 1992). This finding opened a road to the application of a substance having a NOS inhibiting activity to a therapeutic of cerebrovascular diseases.

In the brain region where the blood flow is interrupted, cytotoxic edema occurs first, followed by vasogenic edema. Brain edema is developed several hours after the occurrence of cerebral ischemia and its progress continues for about one week from the onset in clinical settings. Thereafter, the brain edema decreases gradually and, depending on the focal range of infarction, the edema persists as an infarcted area from one to three months. Since the brain is covered with the rigid skull, cerebral edema causes an increase in the brain volume. If the cerebral edema exceeds a certain limit, there occurs an abrupt increase in the tissue pressure and the intracranical pressure, often inducing fatal hernia and eventually aggravating the encephalopathy to determine the scope of the subsequent infarcted area (J. Neurosurg. 77, 169–184, 1992). Thus, the treatment of cerebral edema which is critical to the patient's life and the prognosis of his disease is clinically a very important objective. The three primary methods currently used to treat cerebral edema are hyperpnea, the drainage of cerebrospinal fluid and the use of hypertonic solutions, steroids or the like; however, in almost all cases, these methods provide only temporary ameliorative effect and there is not much promise for the therapeutic efficacy to be finally achieved (J. Neurosurg. 77, 337–354, 1992). Therefore, it has been desirable to develop drugs that have an entirely different mechanism of action and which will prove effective in the treatment of ischemic cerebrovascular diseases.

The present inventors previously found that L-NNA had a capability for ameliorating cerebral edema and infarction that were developed after focal cerebral ischemia (Neurosci. Lett., 147, 159–162, 1992), as well as the neuronal cell death that was developed after global cerebral ischemia (Eur. J. Pharmacol. Env. Tox., 248, 325–328, 1993). However, it has also been reported that relatively high doses of NOS inhibitors are not only ineffective against ischemic brain damage but also they sometimes aggravate the situation (J. Cereb. Blood Flow Metab., 14, 175–192, 1994).

A presently dominant theory based on DNA analyses holds that NOS exists in at least three isoforms, namely, neuronal constitutive NOS (N-cNOS) which is present constitutively in neurons, endothelial constitutive NOS (E-cNOS) which is present constitutively in endothelial cells, and inducible NOS (iNOS) which is expressed on stimulation by cytokines and lipopolysaccharides in macrophages and many other cells. Among these three isoforms, N-cNOS and E-cNOS are calcium-dependent whereas iNOS is calcium-independent (FASEB J. 16, 3051–3064, 1992).

It has become evident that during and shortly after cerebral ischemia there is an excessive accumulation of excitatory amino acids in the extracellular space, and subsequently an increased level of intracellular $Ca^{2+}$, predominantly by way of the N-methyl-D-aspartate (NMDA) class of glutamate receptor activation. These cellular events have a crucial triggering role in the elaboration of ischemic brain damage within the neurons. (J. Cereb. Blood Flow Metab. 1, 155–185, 1981; J. Neurosurg. 60, 883–908, 1984; Trends Neurosci. 11, 465–469, 1988; J. Cereb. Blood Flow Metab. 9, 127–140, 1989). As already mentioned, N-cNOS is calcium-dependent, so inhibiting the hyperactivity of this type of NOS isoform by a particular NOS inhibitor would exhibit neuroprotective effect (Annals Neurol. 32, 297–311, 1992).

Since NO is at least one of EDRF, if E-cNOS is inhibited to less than a certain level, the cerebral blood flow will decrease whereas the blood pressure will increase, thereby aggravating the dynamics of cerebral micro-circulation, possibly leading to an expansion of the ischemic lesion. Therefore, if a therapeutic for ischemic cerebral diseases is to be developed, a NOS inhibitor is desirable that does not inhibit E-cNOS as effectively as N-cNOS (Eur. J. Pharmacol., 204, 339–340, 1991; Proc. Natl. Acad. Sci. USA, 88, 6368–6371, 1991).

Recently and after the date of filing of a product patent application by the present inventors (Feb. 25, 1994), it was reported that δ-(S-methylisothioureido)-L-norvaline, or the claimed compound of the present invention, was capable of inhibiting both N-cNOS and iNOS in a dose-dependent manner [J. Med. Chem. 37, 885–887, 1994 (issue date: Apr. 1, 1994); Advance ACS Abstracts (J. Med. Chem. In abridged form; issue date: Mar. 1, 1994)]. The paper sets forth percent inhibitions of iNOS and cNOS which is equivalent to N-cNOS. However, the paper says nothing about the action on E-cNOS, nor does it make any mention of the potential use of δ-(S-methylisothioureido)-L-norvaline as a therapeutic for cerebrovascular diseases.

DISCLOSURE OF THE INVENTION

The present inventors conducted intensive studies in order to solve the aforementioned problems. As a result, we found that δ-(S-methylisothioureido)-L-norvaline represented by the formula (I):

or salts thereof had a greater N-cNOS inhibiting action than the aforementioned L-NNA and other existing NOS inhibitors and, hence, were effective as therapeutics for cerebrovascular diseases. The present invention has been accomplished on the basis of these findings. Thus, the present invention provides a novel therapeutic for cerebrovascular diseases that involves an entirely different mechanism of action from the existing drugs in that it has a capability for selective inhibition of N-cNOS).

BEST MODE FOR CARRYING OUT THE INVENTION

The compound of the invention can be produced in accordance with the process described in J. Med. Chem. 37, 885–887, 1994, supra; alternatively, the following process may be adopted.

Stated specifically, a compound of the general formula (II):

(where $R_1$ is a lower alkoxycarbonyl group in which the alkyl portion may optionally have a substituent or an optionally substituted lower acyl group; $R_2$ is an optionally substituted straight-chained or branched alkyl group having 1–6 carbon atoms) is hydrolyzed or deprotected by direct treatment with a deprotecting agent so as to produce δ-(S-methylisothioureido)-L-norvaline of the formula (I) or a salt thereof.

In the definition of the general formula (II), examples of the lower alkoxycarbonyl group in which the alkyl portion may optionally have a substituent include a benzyloxycarbonyl group, a 9-fluorenylmethyloxycarbonyl group and a t-butoxycarbonyl group; example of the optionally substituted lower acyl group includes an acetyl group. A particularly preferred example of $R_1$ is a t-butoxycarbonyl group. Examples of the straight-chained or branched alkyl group having 1–6 carbon atoms include methyl, ethyl, benzyl and t-butyl group, preferably the t-butyl group.

The deprotecting reaction is carried out under appropriate conditions depending on the type of the protecting groups used. For example, if $R_1$ is a benzyloxycarbonyl group and $R_2$ is a benzyl group, catalytic reduction may be performed at room temperature in a solvent such as ethyl acetate, methanol or ethanol in the presence of palladium-carbon. Particularly in the case where $R_1$ is a t-butoxycarbonyl group and $R_2$ is a t-butyl group, the reaction is preferably carried out using a deprotecting agent such as trifluoroacetic acid, hydrochloric acid, sulfuric acid or methanesulfonic acid in a solvent that will cause no adverse effects on the reaction such as methylene chloride, ethyl acetate, methanol, ethanol, dioxane or water, or without using any solvent at a temperature ranging from 0° C. to room temperature. The using of trifluoroacetic acid as a deprotecting agent at room temperature under dry conditions is particularly preferred.

Pharmaceutically acceptable salts of the compound (I) include organic acid salts such as acetates, maleates, tartrates, methanesulfonates, benzenesulfonates, formates, p-toluenesulfonates and trifluoroacetates, and inorganic acid salts such as hydrochlorides, sulfates, hydrobromides and phosphates, preferably the dihydrochlorides.

Any pharmaceutically acceptable salts can be used without particular limitations and examples include salts with inorganic acids such as hydrochloric acid, sulfuric acid, nitric acid, hydrobromic acid and phosphoric acid, salts with organic acids such as acetic acid, oxalic acid, tartaric acid, maleic acid, methanesulfonic acid, benzenesulfonic acid, formic acid, p-toluenesulfonic acid and trifluoroacetic acid, mixed salts with alkali metals such as sodium and potassium, and mixed salts with alkaline earth metals such as calcium and magnesium, preferably the dihydrochlorides.

The compound of the invention may be formulated with suitable additives (e.g. excipients, adjuvants, lubricants, antiseptics, disintegrators, buffering agents, binders, stabilizers, wetting agents, emulsifiers, coloring agents, flavoring agents and fragrances) into suitable dosage forms such as tablets, granules, subtilized granules, powders, capsules, syrups, elixirs, suspensions, emulsions and injections, which can be administered either perorally or parenterally, preferably by intramuscular or intravenous injection.

The compound of the invention or salts thereof may be administered in doses that vary with the physical constitution of the patient, his or her age, physical condition, the severity of the disease, the time of lapse after the onset of the disease and other factors; preferably, the daily dose ranges from 0.6 to 60 mg/body.

If the compound of the invention or salts thereof are to be formulated as a preparation for internal application, lactose, sucrose, sorbitol, mannitol, starches such as potato starch or corn starch, starch derivatives and common additives such as cellulose derivatives or gelatin are suitably used as vehicles, with lubricants such as magnesium stearate, carbowaxes and polyethylene glycol being optionally added concurrently; the resulting mixture may be formulated in the usual manner into granules, tablets, capsules or other forms suitable for internal application.

If the compound of the invention or salts thereof are to be formulated as an aqueous preparation, an effective amount of the principal ingredient may be dissolved in distilled water for injection, with antioxidants, stabilizers, dissolution aids, buffering agents, preservatives, etc. added as required and, after a complete solution is formed, it is filtered, filled into ampules, sealed and sterilized by a suitable medium such as high-pressure vapor or dry heat so as to prepare an injection.

If the compound of the invention or salts thereof are to be formulated as a freeze-dried preparation, an aqueous solution having the principal ingredient dissolved in distilled water for injection may be freeze-dried in the usual manner. If necessary, excipients that can be readily freeze-dried such as sugars (e.g. lactose, maltose and sucrose), sugar alcohols (e.g. mannitol and inositol) and glycine may be added to the aqueous solution, which is thereafter freeze-dried in the usual manner.

The following examples are provided for the purpose of further illustrating the production of the compound of the invention but are not in any way to be taken as limiting.

In order to demonstrate the utility of the invention, the selective inhibition of N-cNOS by δ-(S-methylisothioureido)-L-norvaline was tested; in addition, the therapeutic effect of the compound against occlusive cerebrovascular diseases was tested with rats manifesting pathological conditions similar to ischemic cerebral edema and infarction in human.

EXAMPLE 1

Synthesis of δ-(S-Methylisothioureido)-L-Norvaline Dihydrochloride

A mixture of 1.03 g of α-N-t-butoxycarbonyl-δ-(S-methylisothioureido)-L-norvaline-t-butyl ester synthesized as described by Paul L. Feldman (Tetrahedron Lett., 32, 7, 875–878, 1991) and 10 ml of trifluoroacetic acid was stirred at room temperature for 2 h and concentrated under reduced pressure. The residue was dissolved in ethanol (5 ml) and 2 ml of 4N solution of hydrogen chloride in dioxane was added to the ethanol solution at room temperature. Thereafter, the reaction mixture was evaporated. The residue was dissolved in water and freeze-dried to yield δ-(S-methylisothioureido)-L-norvaline dihydrochloride (0.60 g).

$^1$H-NMR (D$_2$O) δ: 1.78–2.36 (4H, m), 2.63 (3H, s), 3.47 (2H, t, J=6.60Hz), 4.17 (1H, t, J=5.97Hz)

FAB-MS (m/z) 206 (M$^+$+1)

TEST EXAMPLE 1

The compound of Example 1 was evaluated for its inhibitory action against N-cNOS and E-cNOS in comparison with previously reported NOS inhibitors.

A crude enzyme sample of N-cNOS was a soluble cytosolic fraction of the rat cerebral cortex whereas a crude enzyme sample of E-cNOS was a homogenate of cow pulmonary arterial endothelium (CPAE) strain.

The following NOS inhibitors were used as control compounds:
L-NNA;
N$^G$-nitro-L-arginine methyl ester (L-NAME);
N$^G$-amino-L-arginine (L-AA);
N$^G$-iminoethyl-ornithine (L-NIO);
N$^G$-monomethyl-L-arginine (L-NMMA);
N$^G$-allyl-L-arginine (L-ALA);
7-nitroindazole (7-NI);
aminoguanidine (AG).

The crude enzyme sample of N-cNOS was prepared by the following procedure. Normal untreated male Sprague-Dawley (SD) rats weighing 300–400 g were decapitated; the whole brain was immediately extracted from each animal and the cerebral cortex was separated on ice. Then, 5 volumes of 50 mM Tris-HCl containing 1 mM DTT (pH 7.4) was added and the mixture was homogenized for 3 min, followed by centrifugation at 1,000×g for 10 min. The supernate was further centrifuged at 100,000×g for 60 min and a soluble cytosolic fraction of the finally obtained supernate was used as the crude enzyme sample of N-cNOS.

The crude enzyme sample of E-cNOS was prepared by the following procedure. CPAE was cultured in a MEM medium containing 20% of FBS. Several days later, the cells were detached from the flask using a solution of 0.25% trypsin containing 1 mM EDTA in 0.1M phosphate-buffered saline (PBS; pH 7.4) and centrifuged at 1,000 rpm for 5 min. The supernate was discarded and upon addition of a suitable amount of PBS, centrifugation was performed at 1,000 rpm for 5 min to wash the cells. The same procedure was repeated using 50 mM Tris-HCl containing 1 mM DTT (pH 7.4) to wash the cells. To the precipitating cells, there was added 50 mM Tris-HCl containing 1 mM DTT (pH 7.4) and the mixture was homogenized for 3 min to yield the crude enzyme sample of E-cNOS.

The method of measuring the NOS activity was basically the same as already reported by the present inventors and consisted of determining quantitatively the conversion of a substrate L-[$^3$H] arginine to a reaction product L-[$^3$H] citrulline [Brain Edema IX (Ito et al. eds.) 60, pp. 285–288, 1994, Acta Neurochir., Springer-Verlag].

The reaction solution consisted of 100 nM L-[$^3$H] arginine, N-cNOS or E-cNOS as crude enzyme sample (6–20 μg/ml protein), 1.25 mM CaCl$^2$, 1 mM EDTA, 10 μ/ml calmodulin, 1 mM NADPH, 100 μM tetrahydrobiopterin, 10 μM FAD, 10 μM FMN and 50 mM Tris-HCl (pH 7.4), to which the compound of the invention or one of the control compounds was added.

The reaction was started by adding L-[$^3$H] arginine to the reaction solution and the mixture was incubated at 37° C. for 10 min. Incubation was terminated by addition of 2 ml of 50 mM Tris-HCl (pH 5.5) containing 1 mM EDTA. The reaction solution was quenched by placing the mixture on ice. The reaction solution was passed through a cation-exchange resin column (Dowex AG50WX-8, Na$^+$ form, 3.2 ml) and the reaction product L-[$^3$H] citrulline was separated from the unreacted residual substrate L-[$^3$H] arginine. The eluant was combined with another eluant resulting from the passage of distilled water (3 ml) through the column and put into a mini vial for recovery of L-[$^3$H] citrulline. Thereafter, 5 ml of a scintillation fluid was added and the contained radioactivity was measured with a liquid scintillation counter to determine the amount of L-[$^3$H] citrulline. The protein concentration of each crude enzyme sample was determined with a micro-assay kit of Biorad Co.

Table 1 lists the values of IC$_{50}$ of all test compounds as their concentrations necessary to inhibit 50% of each NOS isoform activity, as well as the ratio of IC$_{50}$ against E-cNOS to IC$_{50}$ against N-cNOS. All data in Table 1 are expressed by mean±standard error, with the number of cases within parentheses.

From Table 1, one can see the following:
1. The compound of the invention is more potent than the existing NOS inhibitors in inhibiting of N-cNOS;
2. The compound of the invention is capable of highly selective inhibition of N-cNOS in preference to E-cNOS compared to the existing NOS inhibitors (as evidenced by IC$_{50}$ (E-cNOS)/IC$_{50}$ (N-cNOS)=42.5).

TEST EXAMPLE 2

An experiment was conducted to evaluate the effectiveness of the compound of the invention using rats subjected to focal cerebral ischemia. Such models were prepared by occluding the left middle cerebral artery (MCA) in accordance with the method already reported by the present inventors [Neurosci. Lett. 147, 159–162, 1992; Brain Edema IX (Ito et al. eds.) 60, pp. 285–288, 1994, Acta Neurochir., Springer-Verlag].

Ten-week old male SD rats were allowed to inhale 2% halothane (70% $N_2O$ and 30% $O_2$) for inducing anesthesia, then 1% halothane to maintain. Each of thus anesthesized rat was fixed in lateral position on an operating bench. A skin incision was made between the left external auditory pore and the lateral angle of eye and incision was effected along the anterior margin of the temporal muscle down to the zygomatic arch. The temporal muscle, the intraorbital lipid tissue and the eyeball were extracted and submerged in physiological saline containing an antibiotic. To prevent bleeding, the innermost part of the orbit was cauterized with a bipolar coagulator. Under a surgical microscope, the third branch of the trigeminal nerve was identified in the bottommost part of the temporal bone as running inside the lateral muscle and a small hole with a diameter of about 3 mm was opened by means of a dental drill in a position between the foramen oval from which the identified third branch extended and the orbital fissure. A thin layer of the bone was removed by means of a micro-hook and a micro-needle holder. The dura mater and arachnoidea were slightly cut by means of a needle (27G) and a micro-hook and the trunk of the MCA was occluded with a mini-clip for 48 h in the position where the lenticulostriate artery (LSA) branched; alternatively, the same position was occluded for 2 h and then allowed for 2-h reperfusion with the clip removed. During the surgical operation, the temperatures of the right temporal muscle and the rectum were monitored such that they would be kept constant at about 37° C.

In 48-h MCA occlusion models, either the control solvent (physiological saline, 2 ml/kg) or the compound of the invention (0.1, 0.3 or 1 mg/kg) was administered by single-dose application immediately after the MCA occlusion; alternatively, the rats were administered with 24.2 μg/kg of the control solvent or the compound of the invention immediately after the MCA occlusion via a catheter attached to the right femoral vein, followed by sustained administration at a flow rate of 84.2 ng/kg/min. The water content in the brain was measured by the dry-wet method (Neurosci. Lett. 147, 159–162, 1992) in the following manner. Forty-eight hours after MCA occlusion, the rats were decapitated and the left cerebral hemisphere was extracted from each animal within 60 sec; the wet weight of the brain tissue was measured with a chemical balance within 90 sec. Thereafter, the hemisphere was dried in an oven at 105° C. for 3 days and its dry weight was measured. The water content in the brain was determined by the following formula: (wet weight–dry weight)/(wet weight)×100 (%); the results are shown in FIGS. 1 and 2.

In 2-h MCA occlusion, followed by 2-h reperfusion rats, the control solvent (physiological saline, 2 ml/kg) or the compound of the invention (0.1, 0.3 or 1 mg/kg) was administered intraperitoneally immediately after both MCA occlusion and reperfusion. Two hours after the reperfusion, the animals were anesthetized with ether and the brains were perfusion-fixed via the ascending aorta with 4% formaldehyde in phosphate butter (pH 7.4), following a rinse with saline containing 10 units/ml of heparin. Serial coronal sections were sliced 1 mm apart from the frontal lobe and stained with hematoxylin and eosin (Neurosci. Lett., 147, 159–162, 1992; Eur. J. Pharmacol. Env. Tox., 248, 325–328, 1993). The focal area of infarction was determined with an image analyzer according to the following equation: the area of infarction=the normal area in the contralateral hemisphere–the normal area in the affected hemisphere. The result is shown in FIG. 3.

Figure 1:
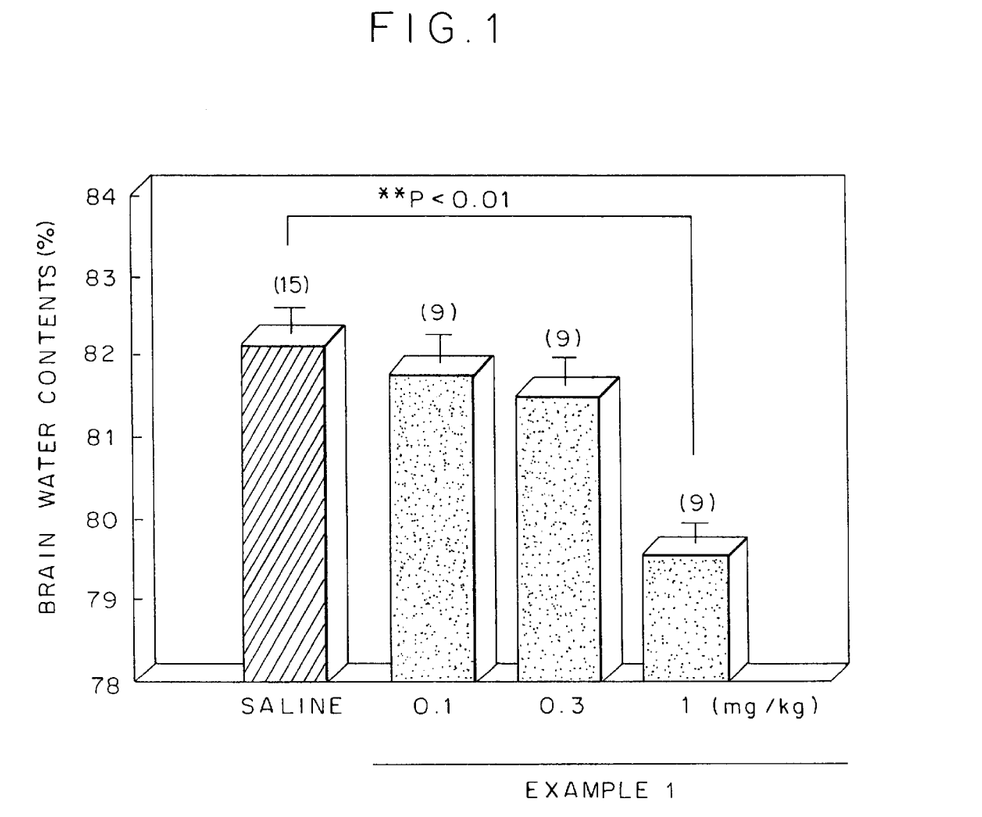
FIG. 1 is a histogram showing how cerebral edema occurring in rats as a result of permanent MCA occlusion could be ameliorated by single intraperitoneal administration of δ-(S-methylisothioureido)-L-norvaline.
Figure 2:
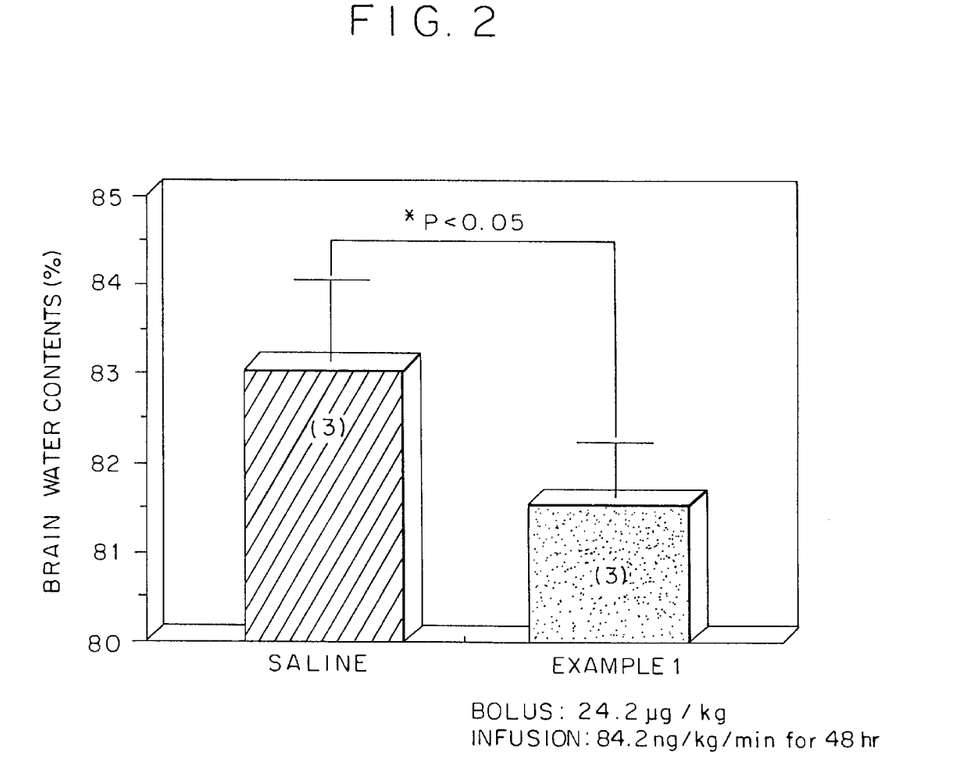
FIG. 2 is a histogram showing how cerebral edema occurring in rats as a result of permanent MCA occlusion could be ameliorated by continuous intravenous administration of δ-(S-methylisothioureido)-L-norvaline.
Figure 3:
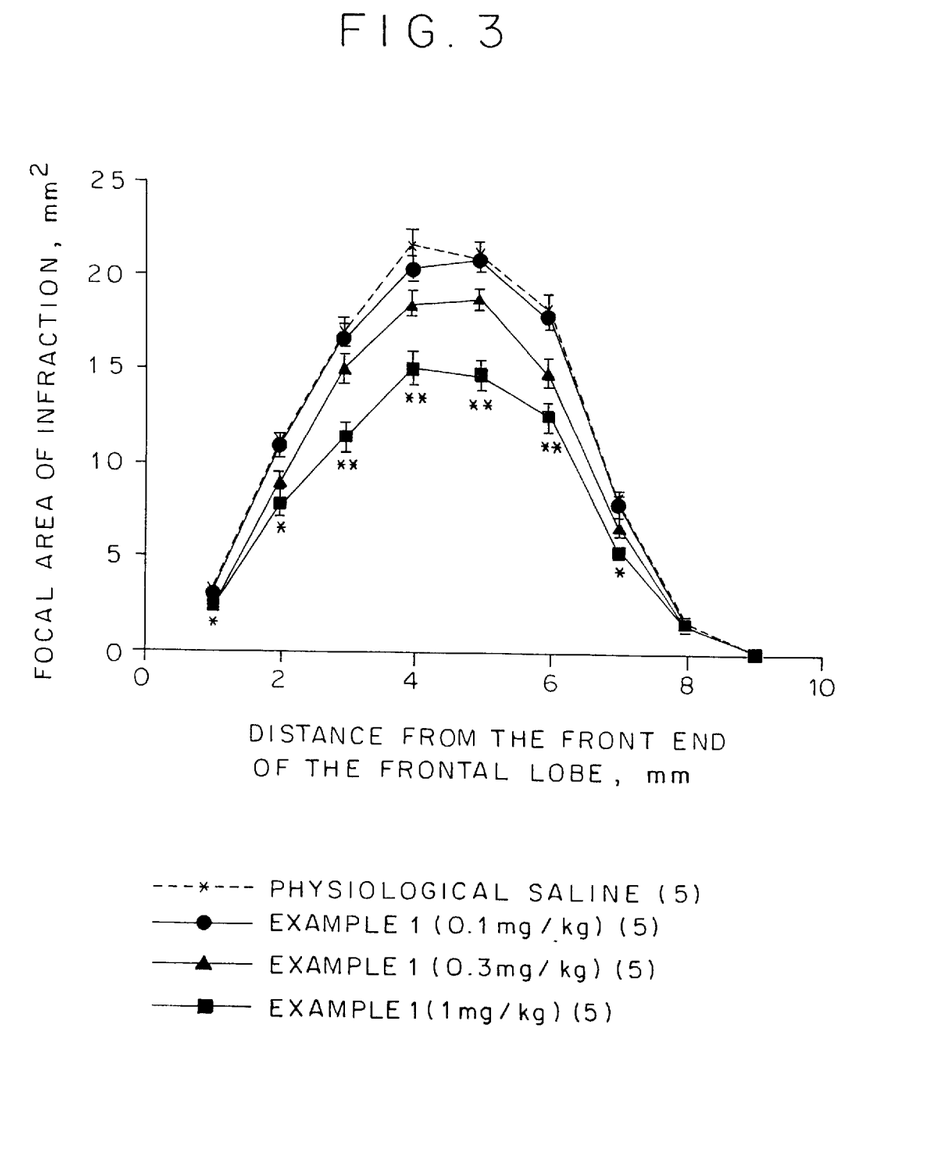
FIG. 3 is a graph showing how cerebral infarction occurring in rats as a result of transient MCA occlusion could be reduced by double intraperitoneal administration of δ-(S-methylisothioureido)-L-norvaline.

All of date in FIGS. 1–3 are expressed by mean±standard error, with the number of animals under test in parenthesis. For statistical analysis, Dunnett's multiple comparative test was conducted and the case having a risk factor (p value) of less than 0.05 was regarded as "statistically significant".

As one can see from FIG. 1, the water content within the left cerebral hemisphere which increased upon 48-h MCA occlusion was reduced in a dose-dependent manner by the single intraperitoneal administration of the compound of the invention; the efficacy of the compound was significant in the group administered 1 mg/kg of the compound.

FIG. 2 shows that the sustained intravenous administration of the compound of the invention was also effective in significantly alleviating the cerebral edema due to 48-h MCA occlusion.

According to FIG. 3, the focus of infarction that was manifested by 2-h MCA occlusion and subsequent 2-h reperfusion could be ameliorated in a dose-dependent manner by the double intraperitoneal administration of the compound of the invention; the efficacy of the compound was significant in the group administered 1 mg/kg of the compound.

INDUSTRIAL APPLICABILITY

δ-(S-methylisothioureido)-L-norvaline is far superior to the existing NOS inhibitors in terms of (1) the N-cNOS inhibiting action and (2) the selectivity for N-cNOS in preference to E-cNOS; hence, the compound is useful as a therapeutic for cerebrovascular diseases.

TABLE 1

| | $IC_{50}$ Values of Test Compounds Against Two NOS Isoforms | | |
|---|---|---|---|
| Test compound | $IC_{50}$ values (nM) | | Ratio of $IC_{50}$ values |
| | N-cNOS (Brain cytosol) | E-cNOS (CPAE) | E-cNOS/N-cNOS |
| Example 1 | 5.6 ± 0.3 (5) | 238.1 ± 82.3 (3) | 42.5 |
| L-NNA | 16.9 ± 3.6 (4) | 89.8 ± 28.7 (3) | 5.3 |
| L-NAME | 79.4 ± 11.6 (3) | 985.4 ± 389.8 (3) | 12.4 |
| L-AA | 152.5 ± 55.7 (3) | 523.5 ± 61.4 (3) | 3.4 |
| L-NIO | 277.0 ± 58.7 (3) | 2,225.5 ± 112.6 (3) | 8.0 |

TABLE 1-continued

IC$_{50}$ Values of Test Compounds Against Two NOS Isoforms

| Test compound | IC$_{50}$ values (nM) | | Ratio of IC$_{50}$ values |
|---|---|---|---|
| | N-cNOS (Brain cytosol) | E-cNOS (CPAE) | E-cNOS/N-cNOS |
| L-NMMA | 337.8 ± 24.7 (3) | 950.7 ± 232.1 (3) | 2.8 |
| L-ALA | 992.0 ± 162.4 (3) | 15,053.4 ± 8,529.6 (3) | 15.2 |
| 7-NI | 4,823.6 ± 985.2 (3) | 2,132.7 ± 793.8 (3) | 0.4 |
| AG | 20,262.9 ± 4,172.6 (3) | >100,000 (3) | >4.9 |

We claim:

1. A method of treating a subject having cerebral edema, or of prophylaxis of cerebral edema in a subject diagnosed as being at risk therefor, comprising administering to said subject a therapeutically effective amount of a pharmaceutical composition that contains δ-(S-methylisothioureido)-L-norvaline, which selectively inhibits neuronal constitutive nitric oxide synthase (N-cNOS) in preference to endothelial constitutive nitric oxide synthase (E-cNOS) as indicated by an IC$_{50}$ (E-cNOS) to IC$_{50}$ (N-cNOS) ratio of at least 30, said pharmaceutical composition further comprising a pharmaceutically acceptable carrier.

* * * * *

(12) REEXAMINATION CERTIFICATE (4270th)
United States Patent
Makino et al.

(10) Number: US 5,869,526 C1
(45) Certificate Issued: Feb. 6, 2001

(54) δ-(S-METHYLISOTHIOUREIDO)-L-NORVALINE THERAPEUTIC FOR CEREBROVASCULAR DISEASES HAVING NITRIC OXIDE SYNTHASE INHIBITING FACTOR (75) Inventors: Toshihiko Makino; Toshiaki Nagafuji, both of Shizuoka-ken (JP)

(73) Assignee: Chugai Seiyaku Kabushiki Kaisha, Tokyo (JP)

Reexamination Request:
No. 90/005,737, Jun. 5, 2000

Reexamination Certificate for:
Patent No.: 5,869,526
Issued: Feb. 9, 1999
Appl. No.: 08/696,866
Filed: Aug. 21, 1996

(22) PCT Filed: Feb. 23, 1995
(86) PCT No.: PCT/JP95/00265
  § 371 Date: Aug. 21, 1996
  § 102(e) Date: Aug. 21, 1996
(87) PCT Pub. No.: WO95/22968
  PCT Pub. Date: Aug. 31, 1995

(30) Foreign Application Priority Data
Feb. 25, 1994 (JP) .................................. 6-66386
Aug. 12, 1994 (JP) .................................. 6-222396

(51) Int. Cl.$^7$ ...................................... A61K 31/21
(52) U.S. Cl. .................................. 514/508; 558/5
(58) Field of Search .......................... 514/508; 558/5

(56) References Cited

FOREIGN PATENT DOCUMENTS

WO 95/09619   4/1995   (WO).
WO 95/13804   5/1995   (WO).

*Primary Examiner*—Floyd D. Higel (57) ABSTRACT

Compound represented by the formula (I):

or pharmaceutically acceptable salts thereof, as well as therapeutics for cerebrovascular diseases containing such compounds or salts as an active ingredient. The compounds are capable of selective inhibition of nitric oxide synthase in neurons and, hence, are useful as the active ingredient of therapeutics for cerebrovascular diseases.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 1 is confirmed.

* * * * *